United States Patent [19]

Mentech et al.

[11] Patent Number: 5,543,512
[45] Date of Patent: Aug. 6, 1996

[54] METHOD FOR PREPARING SACCHARIDE MONOMERS COMPRISING AT LEAST ONE POLYMERIZABLE CARBONYL-OXYVINYL GROUP

[75] Inventors: Julio Mentech; Isabelle Betremieux; Bruno Legger, all of Villeurbanne, France

[73] Assignee: Beghin-Say, Thumeries, France

[21] Appl. No.: 378,707

[22] Filed: Jan. 26, 1995

Related U.S. Application Data

[63] Continuation of Ser. No. 838,737, Mar. 13, 1992, abandoned.

[30] Foreign Application Priority Data

Jul. 16, 1990 [FR] France .................. 90 09015

[51] Int. Cl.[6] .................. C07H 13/02; C07H 1/00
[52] U.S. Cl. .................. 536/115; 536/116; 536/119; 536/124
[58] Field of Search .................. 536/119, 115, 536/116, 124

[56] References Cited

U.S. PATENT DOCUMENTS

| | | | |
|---|---|---|---|
| 4,328,337 | 5/1982 | Kawasaki et al. | 536/119 |
| 4,451,629 | 5/1984 | Tanaka et al. | 526/238.23 |
| 4,465,827 | 8/1984 | Kawasaki et al. | 536/119 |
| 4,833,202 | 5/1989 | Dunn | 526/238.23 |
| 5,164,492 | 11/1992 | Kitazawa et al. | 536/116 |

OTHER PUBLICATIONS

Journal of the American Chemical Society, vol. 72, No. 3, issued 23 Mar. 1950, Morris Zief, "Unsaturated Esters of Sucrose", pp. 1137–1140.
Gruber, *Monatshefte für Chemie* 112, 273–285 (1981).
Black et al, Die Makromolekulare Chemie 117 (1968) 210–214 (No. 2817).

*Primary Examiner*—John Kight, III
*Assistant Examiner*—Everett White
*Attorney, Agent, or Firm*—Breiner & Breiner

[57] ABSTRACT

The invention concerns a process for preparing saccharide monomers comprising at least one polymerizable acrylate or methacrylate group whereby the saccharide used in the process is selected from mono-, di- and tri-saccharides, in particular from non-reducing mono-, di- and tri-saccharides. The process comprises reacting the saccharide in an aqueous medium with an esterifying reagent containing the polymerizable acrylate or methacrylate group in the presence of a base while maintaining the pH of the reaction medium to a value within the range of 7 to 11 during the entire reaction time. The invention furthermore concerns saccharide monomers comprising at least one polymerizable acrylate or methacrylate group with a controlled degree of substitution.

32 Claims, No Drawings

5,543,512

METHOD FOR PREPARING SACCHARIDE MONOMERS COMPRISING AT LEAST ONE POLYMERIZABLE CARBONYL-OXYVINYL GROUP

This is a continuation of application Ser. No. 07/838,737 filed on Mar. 13, 1992, now abandoned.

The present invention concerns a new method for preparing saccharide monomers comprising at least one polymerizable carbonyl-oxyvinyl group. In particular, the invention relates to direct and controlled preparation methods of acrylic-type esters of saccharides selected from the mono-, di- and tri-saccharides, in particular the non-reducing mono-, di- and tri-saccharides, employing an aqueous reaction medium.

The invention also concerns new saccharide monomers comprising at least one polymerizable carbonyl-oxyvinyl group and having a controlled degree of substitution.

Saccharide monomers comprising at least one polymerizable carbonyl-oxyvinyl group are used foremost in polymer technology following homo- and co-polymerization with various co-monomers.

Various procedures of preparing acrylic-type esters of saccharides have already been carried out, but none has been found to be satisfactory. These procedures as a rule require preliminary stages which protect certain reactive functions of the initial saccharide molecule in order to permit selective modification of the residual functions which are to be esterified. The intermediate stages entail long and costly syntheses which preferably are avoided. Such reactions are described in particular in the following publications: T. P. Bird et al, *J. Chem. Soc.* (1966) 1913–18, (1); W. A. P. Black et al, *Carbohyd. Res.*, 5 (1967) 362–365 (2); W. A. P. Black et al, *Makromol. Chem.*, 117 (1968) 210 (3); W. A. P. Black et al, *J. Chem. Soc.*, (1963) 4433 (4). Furthermore, the patents EP 180,262; EP 237,131; EP 237,132, and U.S. Pat. No. 4,721,760 of Shell Oil Company describe the synthesis of water-soluble polymers prepared by polymerizing a saccharide monomer, i.e., 3–0 methacrylate of glucose, which is synthesized by procedures described in the above publications.

Other procedures for preparing acrylic-type saccharide esters are known which are more direct. In particular, such procedures are described in the following publications: E. Avela et al, "Sucrochemistry," Washington, *American Chemical Society*, 1977, S. 62 (ACS Symposium Series No. 41); H. Graber, *Monatsch. Chem.*, (1981) 112, 273–85. However, such reactions entail polar aprotic solvents (DMF, DMSO, pyridine, etc.) which involve additional problems due to their cost, toxicity, inflammability, etc.

When the selected acrylic type of saccharide esters are in the form of monomers and comonomers, it is also necessary to precisely control the degree of substitution of the substrate molecule. If the average degree of substitution of the particular monomer is larger than approximately 1, there will be some crosslinking during its polymerization. The crosslinking rate in turn affects various (physical, chemical, etc.) properties of the polymers that are so made.

Moreover, it may be desirable, for instance when the monomers in question are desired to produce thermoplastic copolymers, that they be linear, in other words, that their crosslinking rate be zero. The manufacture of such linear polymers, therefore, requires to have available ester monomers of the acrylic type of saccharide with a degree of substitution very close to 1, and hence to have available a procedure for preparing acrylic-type saccharide esters which allow control of their degree of substitution. Such a control was achieved using the above-mentioned indirect manufacturing procedures. Such, however, can not be carried out industrially in the light of their aforementioned many drawbacks.

The direct procedures listed above again do not allow satisfactory control of the degree of substitution and, in any event, the use of organic solvents which they require makes them virtually commercially impractical.

One object of the present invention is to provide a method for preparing monomers comprising at least one polymerizable carbonyl-oxyvinyl group, that is acrylic-type esters of saccharides, in a single stage without the need of organic solvents.

Another object of the invention is to prepare acrylic-type esters of saccharides with excellent control of their degree of substitution.

Yet another object of the invention is to manufacture acrylic-type esters of saccharides having a degree of substitution substantially equal to 1.

The present method provides a method for preparing monomers comprising at least one polymerizable carbonyl-oxyvinyl group, in particular acrylic-type esters of saccharides meeting the above objectives.

Accordingly, the present invention provides a method for preparing monomers comprising at least one polymerizable carbonyl-oxyvinyl group, in particular of acrylictype esters of saccharides, which consist of reacting in an aqueous medium the saccharide with an esterifying reagent in the presence of a base, keeping the pH at a value in the range of 7 to 11 during the entire time of reaction.

The initial saccharide is selected from the mono-, di- and tri-saccharides, in particular from the non-reducing mono-, di- and tri-saccharides. Such a saccharide illustratively is saccharose.

The polymerizable carbonyl-oxyvinyl group, which is derived from an acrylic-type compound, for instance, is an acryloyl, methacryloyl group, etc.

The esterifying reagent is selected from the halides, for instance the acyl chlorides, the alkyl esters which have an alkyl group with from 1 to 3 carbon atoms such as acyl methyl, and ethyl esters, acyl anhydrides, the acyl radical for instance being an acrylic, methacrylic, etc., radical.

The base may be organic or, preferably, mineral. The bases which can be used in the invention illustratively, but not restrictively, include $Na_2CO_3$, $K_2CO_3$, NaOH, KOH.

During the entire reaction time, the pH-value must be kept within the range of from 7 to 11, preferably between 10 and 11.

The reaction time is easily ascertained by one skilled in the art, in particular as a function of the desired degree of substitution, taking into account the values of the other reaction parameters. Care must be taken to avoid excessively long reaction times which may enhance hydrolytic inverse reactions of the formed esters.

The reaction can be carried out at atmospheric pressure and a temperature of from 0° C. to about 60° C., preferably from about 0° C. to about 30° C.

The molar ratio of the esterifying reagent to the initial saccharide is a significant reaction parameter. In order to obtain mono-substituted products, the molar ratio of esterifying reagent to saccharide shall be approximately 0.1 to 8, preferably 0.2 to 2, and most preferably about 0.2 to 1.5. The value of the molar ratio must exceed 8 to obtain more substituted products.

It may be necessary to stabilize the reagents and/or the products during their preparation or during any subsequent purification stage. Illustratively, such stabilization may be achieved by adding a conventional polymerization inhibitor, such as 2,6-di-tert-butyl-4-methylphenol which is commercially sold as "Ionol" by the Shell Chemical Company; benzoquinone, etc.

As already mentioned above, and in the manner elucidated below in the examples, the contents in mono- or poly-substituted products shall be in the majority depending on the selected conditions.

The method of the invention allows preparing in a controlled manner both products with a degree of substitution substantially equal to 1 and products with a degree of substitution larger than 1.

It is desirable in some applications to reduce as much as possible the proportion of the monomer polysubstituted products in order to be able to prepare, for instance, linear polymers. In that case, appropriate purification will be carried out. For this purpose, use may be made of conventional purification procedures, in particular chromatography or fractionated crystallization, or preferably liquid-liquid extraction.

When employing liquid-liquid extraction, in a first step, the polysubstituted derivatives that were formed simultaneously with the desired mono-substituted derivatives are extracted from the aqueous reaction medium by an organic solvent or a mixture of organic solvents, such as methylethyl ketone, 2-butanol, etc.

In a second step, another combination of extracting solvents is used which, as a rule, is more polar, illustratively n-butanol, 2-butanol, isopropanol, ethanol-methanol mixtures, so that the desired mono-substituted products can be extracted.

During this second purification step, a certain quantity of unreacted, initial saccharide is extracted along with the desired mono-substituted monomer derivative. This fact does not affect the subsequent polymerization of the monomer because of the inert nature of the free saccharide during polymerization.

The organic phases containing the desired products are stabilized using a suitable polymerization inhibitor and are evaporated at reduced pressure to become dry products.

Before the monomers so prepared are polymerized, the product preferably is washed with an organic solvent, such as hexane, ether, $CH_2Cl_2$, etc., to eliminate the previously added inhibitor.

The method of the present invention allows manufacturing, in an aqueous medium, of saccharide monomers comprising at least one polymerizable carbonyl-oxyvinyl group, with excellent control of their degree of substitution; and it may furthermore lead to achieving saccharide carbonyl-oxyvinyl monomers with a degree of substitution substantially equal to 1, that is between 1 and about 1.1.

The following examples illustrate the invention without thereby implying restriction.

EXAMPLE 1

25 g of saccharose (73 mM) are introduced into 75 ml of water inside a 250 ml reactor. The solution pH is adjusted to 10.5 using 6N soda, and this value is maintained during the entire reaction. 3 ml (36.5 mM) of acryloyl chloride are dripped-in with agitation and at ambient temperature. After 15 minutes, the reaction medium is neutralized.

The composition of organic products in the crude reaction mixture is shown by thin-layer chromatography to be the following:

unreacted saccharose 60% saccharose monoacrylates: 20% saccharose polyacrylates: 20%

The molar distribution of the purified fraction (12 g) in saccharose monoacrylates following several extractions and after HPLC analysis is as follows:

saccharose : 53% saccharose monoacrylates: 47%

EXAMPLE 2

25 g (73 mM) of saccharose are introduced into ml of water inside a 250 ml reactor. The solution pH is adjusted to 10.5 using 6N soda, and this value is maintained during the entire reaction. 8 ml (73 mM) of methacryloyl chloride are dripped-in with agitation and at ambient temperature. At the end of dripping, the reaction medium is neutralized.

The saccharose conversion rate (CR) and the composition of the crude reaction mixture in organic products as determined by CCM and HPLC analyses are the following:

CR (saccharose): 54% unreacted saccharose: 40% saccharose monomethacrylates: 40% saccharose polymethacrylates: 20%

EXAMPLE 3

Example 2 above was repeated using the following quantities:

| saccharose | 25 g | (73 mM) |
| methacryloyl chloride | 4 ml | (36.5 mM) |
| 6N soda | | | in 75 ml of water. The following results were obtained:

CR (saccharose): 35% unreacted saccharose: 50% saccharose monomethacrylates: 35% saccharose polymethacrylates: 15%

EXAMPLE 4

Example 2 above was repeated using the following quantities:

| saccharose | 250 g | (730 mM) |
| methacryloyl chloride | 2 ml | (180 mM) |
| 6N soda | | | in 750 ml water. The following results were obtained:

CR (saccharose): 24% unreacted saccharose: 70% saccharose monomethacrylates: 25% saccharose polymethacrylates: 5%

EXAMPLE 5: Purifying saccharose monomethacrylates by liquid-liquid extraction.

The crude reaction mixture prepared in above Example 4 was saturated with sodium chloride and was extracted with mixtures of methyl-ethyl ketone and butanol-2 (50/50; 2 ×0.5 liter) to extract the polymethacrylates; then with butanol-2 (6×0.5 liter) to obtain, following evaporation of the butanol-2 and in the presence of about 2%-weight of 2,6-di-ter-butyl-4-methylphenol (Ionol) as monomethacrylate stabilizer, a mixture (75 g) containing saccharose monomethacrylates (80%) and saccharose (20%), without polymethacrylates, and enriched in monomethacrylates relative to the processed crude reaction medium.

The Ionol used to stabilize the monomethacrylate fraction may be removed before polymerization by repeated washing with dichloromethane.

EXAMPLE 6: Purifying saccharose monomethacrylates by chromatography.

30 g of the product from the above Example 4 were chromatographed on a silica column MATREX™ SILICA Si (35–78 μm) using as the eluent a mixture of chloroform/acetone/methanol/water of 40/20/30/10. The fraction containing the saccharose monomethacrylates was evaporated at reduced pressure in the presence of an inhibitor. 6.5 g (22% yield) of a white, amorphous solid was obtained.

Centesimal Analysis: theory 46.80% C; 6.34% H measured 46.42% C; 6.12% H

EXAMPLE 7

The crude reaction mixture obtained from the above Example 2 was saturated with NaCl and then extracted with butanol-2 (8×50 ml). The first three extracts rich in polymethacrylates were put together and evaporated in the presence of 3% Ionol to arrive at a fraction (10 g) enriched in polymethacrylate and containing 70% saccharose polymethacrylates and 30% saccharose monomethacrylates.

EXAMPLE 8

25 g (73 mM) of saccharose are dissolved in 75 ml water. The solution pH is adjusted to 10.5 using 6N soda and is kept at that level during the entire reaction. 2.5 ml (18 mM) of methacrylic anhydride are dripped-in with agitation and at ambient temperature, and thereupon the reaction medium is neutralized. The following results were obtained:

saccharose CR: 24% unreacted saccharose: 70% saccharose monomethacrylates: 25% saccharose polymethacrylates: 5%

EXAMPLE 9

25 g (73 mM) of saccharose are dissolved in 75 ml water. The solution pH is adjusted to 10.5 using 6N soda and is kept at that value during the entire reaction time. 7.75 ml (72 mM) of methyl methacrylate are dripped-in while agitating for 6 h at ambient temperature. The mixture is purified by chromatography (see above Example 2) and 0.8 g (3% yield.) of saccharose monomethacrylates are collected.

EXAMPLE 10: Acetylating saccharose monomethacrylates.

2 g (4.9 mM) of saccharose monomethacrylates are dissolved in 20 ml pyridine and 10 ml of acetic anhydride at 0° C. are dripped-in. The reaction medium is kept agitated for 12 h at ambient temperature and then is evaporated. The residue so obtained is treated with 20 ml water and 4×20 ml ether. The etherified phase is treated with an aqueous phase of HCl (1N) and of (saturated) $Na_2CO_3$, which is followed by rinsing with water, drying, and evaporating. The expected products were obtained in a quantitative yield.

EXAMPLE 11: Purifying the saccharose monomethacrylates by silica chromatographic column.

The saccharose monomethacrylates were analyzed by high-performance liquid chromatography under the following conditions: column L=25 cm, inside diameter=4.6 mm; Nucleosil $NH_2$ 5 μm with an eluent composed of $CH_3CN/H_2O$=75/25; and flow=1 ml/min, infrared detector. The capacity factors are—

$$\text{saccharose } k' = \frac{t - t_0}{t_0} \times 1.94$$

saccharose monomethacrylates k'=0.37

The saccharose monoacrylates and monomethacrylates of the above examples evince a purity higher than 95% as measured by HPLC and proton RMN.

We claim:

1. A process for preparing monomers including at least one polymerizable acrylate or methacrylate group and having a controlled degree of substitution, comprising reacting in one single, direct and controlled stage, a saccharide selected from the group consisting of monosaccharides, disaccharides and trisaccharides, in an aqueous medium with an esterifying reagent containing a polymerizable group derived from an acrylic-type compound in the presence of a mineral base such that pH of the reaction medium is maintained at a value within a range of 7 to 11 during reaction; and recovering the monomers.

2. The process according to claim 1 wherein said saccharide is a non-reducing saccharide.

3. The process according to claim 1 wherein said polymerizable group derived from an acrylic-type compound is an acryloyl or methacryloyl group.

4. The process according to claim 1 wherein said esterifying reagent is a halide.

5. The process according to claim 4 wherein said halide is a chloride.

6. The process according to claim 1 wherein said esterifying reagent is selected from alkyl esters wherein the alkyl group comprises 1 to 3 carbon atoms and anhydrides of said alkyl esters.

7. The process according to claim 1 wherein said saccharide is sucrose and the pH value is maintained in the range of 10 to 11.

8. The process according to claim 1 wherein the molar ratio of said esterifying reagent to said saccharide is between about 0.1 and 8.

9. The process according to claim 8 wherein said molar ratio is between about 0.2 and 2.

10. The process according to claim 9 wherein said molar ratio is between about 0.2 and 1.5.

11. The process according to claim 1 wherein said mineral base is selected from the group consisting of $Na_2CO_3$, $K_2CO_3$, NaOH and KOH.

12. The process according to claim 1 further comprising purifying the monomers produced prior to recovering the monomers.

13. The process according to claim 12 wherein said purifying of the monomers is carried out by chromatography or fractionated crystallization.

14. The process according to claim 12 wherein said purifying of the monomers is carried out by liquid-liquid extraction.

15. The process according to claim 14 wherein said liquid-liquid extraction includes a first stage involving extracting with at least one organic solvent and a second stage involving extracting with a combination of solvents different from those utilized in said first stage.

16. The process according to claim 1 wherein the reagent and/or the monomers prepared are stabilized.

17. The process according to claim 16 wherein said stabilization is implemented using a polymerization inhibitor.

18. The process according to claim 17 wherein said polymerization inhibitor is benzoquinone or 2,6-di-tert-butyl-4-methyl-phenol.

19. A process for preparing monomers including at least one polymerizable acrylate or methacrylate group and having a controlled degree of substitution between 1 and 1.1, comprising reacting in one single, direct and controlled stage, a saccharide selected from the group consisting of monosaccharides, disaccharides and trisaccharides, in an aqueous medium with an esterifying reagent containing a polymerizable group derived from an acrylic-type compound, the molar ratio of said esterifying reagent to said saccharide being approximately between 0.2 and 1.5, in the presence of a mineral base such that pH of the reaction medium is maintained at a value within a range of 7 to 11 during reaction; purifying the monomers produced; and recovering the monomers.

20. The process according to claim 19 wherein said saccharide is a non-reducing saccharide.

21. The process according to claim 19 wherein said polymerizable group derived from an acrylic-type compound is an acryloyl or methacryloyl group.

22. The process according to claim 19 wherein said esterifying reagent is a halide.

23. The process according to claim 22 wherein said halide is a chloride.

24. The process according to claim 19 wherein said esterifying reagent is selected from alkyl esters wherein the alkyl group comprises 1 to 3 carbon atoms and anhydrides of said alkyl esters.

25. The process according to claim 19 wherein said saccharide is sucrose and the pH value is maintained in the range of 10 to 11.

26. The process according to claim 19 wherein said mineral base is selected from the group consisting of $Na_2CO_3$, $K_2CO_3$, NaOH and KOH.

27. The process according to claim 19 wherein said purifying of said monomers is carried out by chromatography or fractionated crystallization.

28. The process according to claim 19 wherein said purifying of said monomers is carried out by liquid-liquid extraction.

29. The process according to claim 28 wherein said liquid-liquid extraction includes a first stage involving extracting with at least one organic solvent and a second stage involving extracting with a combination of solvents different from those utilized in said first stage.

30. The process according to claim 19 wherein the reagent and/or the monomers prepared are stabilized.

31. The process according to claim 30 wherein said stabilization is implemented using a polymerization inhibitor.

32. The process according to claim 31 wherein said polymerization inhibitor is benzoquinone or 2,6-di-tert-butyl-4-methyl-phenol.

* * * * *